(12) United States Patent
Jakkula et al.

(10) Patent No.: US 8,725,284 B2
(45) Date of Patent: May 13, 2014

(54) MOISTURE MEASUREMENT (75) Inventors: Pekka Jakkula, Oulu (FI); Markku Seppänen, Kuluntalahti (FI); Mikko Vuolteenaho, Kiiminki (FI)

(73) Assignee: Senfit Oy, Oulu (FI)

( * ) Notice: Subject to any disclaimer, the term of this patent is extended or adjusted under 35 U.S.C. 154(b) by 0 days.

(21) Appl. No.: 13/503,724

(22) PCT Filed: Nov. 3, 2010

(86) PCT No.: PCT/FI2010/050881
§ 371 (c)(1),
(2), (4) Date: May 31, 2012

(87) PCT Pub. No.: WO2011/055015
PCT Pub. Date: May 12, 2011

(65) Prior Publication Data
US 2012/0239210 A1 Sep. 20, 2012

(30) Foreign Application Priority Data
Nov. 6, 2009 (FI) .................................... 20096149

(51) Int. Cl.
G06F 19/00 (2011.01)
G01R 27/04 (2006.01)

(52) U.S. Cl.
USPC ............................ 700/207; 700/274; 324/634

(58) Field of Classification Search
None
See application file for complete search history.

(56) References Cited

U.S. PATENT DOCUMENTS

| 5,291,422 | A | * | 3/1994 | Esztergar ........................ 702/30 |
| 5,392,118 | A | * | 2/1995 | Wickramasinghe .......... 356/496 |
| 5,453,692 | A | * | 9/1995 | Takahashi et al. ............. 324/318 |
| 5,942,991 | A | * | 8/1999 | Gaudreau et al. ........ 340/870.16 |
| 7,423,435 | B2 | * | 9/2008 | Sawamoto et al. ............ 324/644 |
| 7,786,938 | B2 | * | 8/2010 | Sorvala et al. .......... 343/700 MS |
| 2003/0231086 | A1 | * | 12/2003 | Ishikawa et al. ............ 333/219.1 |
| 2004/0124853 | A1 | | 7/2004 | Moller et al. |
| 2004/0166387 | A1 | * | 8/2004 | Imamura et al. ................. 429/22 |

(Continued)

FOREIGN PATENT DOCUMENTS

| EP | 0372992 A2 | 6/1990 |
| EP | 0665426 A1 | 8/1995 |

(Continued)

OTHER PUBLICATIONS

Kimmo Aho, International Search Report for corresponding International Application No. PCT/FI2010/050881, p. 1-5 (Feb. 28, 2011).

(Continued)

*Primary Examiner* — Sean Shechtman
(74) *Attorney, Agent, or Firm* — Hoffmann & Baron, LLP (57) ABSTRACT

An electromagnetic field tuning and detection apparatus generates in to a material space and in at least two different directions radio frequency electromagnetic fields adapted to resonate in different directions at a different frequency on the basis of a material insertable into the material space; and a signal processing unit configured to determine a moisture content of the material on the basis of a resonance frequency of each electromagnetic field and quality of each resonance in different directions. While controlling a process, a control system comprises a measurement chamber and an electromagnetic field tuning and detection apparatus placed on each material feed line of the process. A controller may control the process on the basis of each determined moisture content on each feed line.

33 Claims, 8 Drawing Sheets

(56) References Cited

U.S. PATENT DOCUMENTS

2007/0074580 A1* 4/2007 Fallah-Rad et al. ............ 73/786
2008/0081234 A1* 4/2008 Winkler ........................ 429/22
2009/0009189 A1* 1/2009 Herrmann et al. ............ 324/634

FOREIGN PATENT DOCUMENTS

| EP | 0718555 | A1 | 6/1996 |
| EP | 1734361 | A1 | 12/2006 |
| FI | 74816 | | 11/1987 |
| WO | WO0012974 | A1 | 3/2000 |

OTHER PUBLICATIONS

Laura Salmi, Finnish Search Report for corresponding Finnish Application No. 20096149, p. 1-2 (Jun. 29, 2010).

* cited by examiner

$D_y = D_x + \Delta_1$
$D_z = D_x + \Delta_2$

MOISTURE MEASUREMENT

CROSS-REFERENCE TO RELATED APPLICATIONS

This application is a National Stage application of International Application No. PCT/FI2010/050881, filed Nov. 3, 2010, which claims benefit to Finnish Application No. 20096149, filed Nov. 6, 2009, which are incorporated by reference herein in their entirety.

BACKGROUND

1. Field

The invention relates to a measurement device, a control system, and a measurement and control method.

2. Description of the Related Art

Measurement of moisture of materials of natural origin is important e.g. in energy production plants burning biomaterials. Measurement of moisture of materials is necessary also in other processes. Examples of such processes include pulp cooking processes and Thermo Mechanical Pulp (TMP) processes wherein wood chips are refined. Furthermore, moisture may be measured e.g. from various minerals.

Radio frequency electromagnetic radiation may be used for measuring moisture of various materials. Moisture determination is, however, problematic. Owing e.g. to the dielectric anisotropy, density, shape and size and/or non-homogeneity of pieces or samples of the material to be measured, a measurement result is highly direction-dependent. Such problems impede measurement and make measurement by radio frequency electromagnetic radiation inaccurate and unreliable.

SUMMARY

An object of the invention is to provide an improved solution for measuring moisture. This is achieved by a measurement device for measuring moisture from a direction-dependent material by electromagnetic radiation. The measurement device comprises an electromagnetic field tuning and detection apparatus configured to generate in to a material space and in at least two different directions radio frequency electromagnetic fields adapted to resonate in different directions at a different frequency on the basis of the material insertable into the material space; and a signal processing unit configured to determine a moisture content of the material on the basis of a resonance frequency of each electromagnetic field and quality of each resonance in different directions.

The invention also relates to a control system for controlling a process which receives a direction-dependent material whose moisture content varies. The control system comprises one or more electromagnetic field tuning and detection apparatuses adapted to be placed on each material feed line of the process, the electromagnetic field tuning and detection apparatus being configured to generate, at least in two different directions, radio frequency electromagnetic fields adapted to resonate in different directions at a different frequency on the basis of a material insertable into a material space; a signal processing unit configured to determine a moisture content of the material on each feed line on the basis of a resonance frequency of each electromagnetic field and quality of each resonance in each direction; and a controller configured to control the process on the basis of each determined moisture content on each feed line.

The invention also relates to a method of measuring moisture from a direction-dependent material by radio frequency electromagnetic radiation. The method further comprises generating at least in two different directions radio frequency electromagnetic fields that resonate in different directions at a different frequency on the basis of the material insertable into a material space; and determining a moisture content of the material on the basis of a resonance frequency of each electromagnetic field and quality of each resonance in orthogonal directions.

The invention still further relates to a method of controlling a process which receives a direction-dependent material whose moisture content varies. The method further comprises generating in to a measurement chamber at least in two different directions radio frequency electromagnetic fields that resonate in different directions at a different frequency on the basis of the material insertable into the material space; determining the moisture content of the material on the basis of a resonance frequency of each electromagnetic field and quality of each resonance in different directions; and controlling the process on the basis of each determined moisture content on each feed line.

Preferred embodiments of the invention are described in the dependent claims.

The solution according to the invention enables several advantages to be achieved. The direction-dependence of measurement is eliminated or substantially reduced and the measurement becomes reliable.

BRIEF DESCRIPTION OF THE DRAWINGS

The invention is now described in closer detail in connection with the preferred embodiments and with reference to the accompanying drawings, in which.

DETAILED DESCRIPTION

In the present application, direction-dependence refers to the macroscopic, microscopic and/or molecular orientation of the material to be measured. The direction-dependence of a material means that a physical property of the material, and thus also the measured result, changes according to the measurement direction. Such a physical property may be the material's density, refractive index, homogeneity, scattering of radiation caused by the material, damping, projection surface area of pieces or particles contained in the material in the measurement direction, etc. Said properties may also depend on one another. For instance, the projection surface area of the pieces and/or particles in the material affects the scattering of radiation and thus the damping of radiation as well.

Macroscopic orientation may mean e.g. that the material contains separate pieces, most of which settle parallelly or codirectionally according to their shape. In such a case, for instance, bar-like pieces settle such that for most of such pieces, the longitudinal axis codirectional with the bar is parallel. The pieces may be plant stems, trunks, branches, wood chips, bark, etc. A macroscopic piece refers to a piece of material visible to the naked eye.

Microscopic orientation may mean e.g. that the material comprises separate particles, most of which settle parallelly or codirectionally according to their shape. In such a case, for instance, fibrous particles settle such that for most of the particles, the longitudinal axis codirectional with a fibre is parallel. The particles may be e.g. plant fibres or cells. In normal viewing conditions, no single microscopic particle is visible to the naked eye.

Molecular orientation may mean dielectric anisotropy of a material. In a crystal, the environment of an atom or a molecule is not necessarily spherically symmetrical. The molecules of the material may be e.g. polarized, which means that an electric field behaves differently in different directions.

The different orientations result in a material having a common anisotropy which affects the electric field and produces different results when measurements are carried out in different directions.

Figure 1:
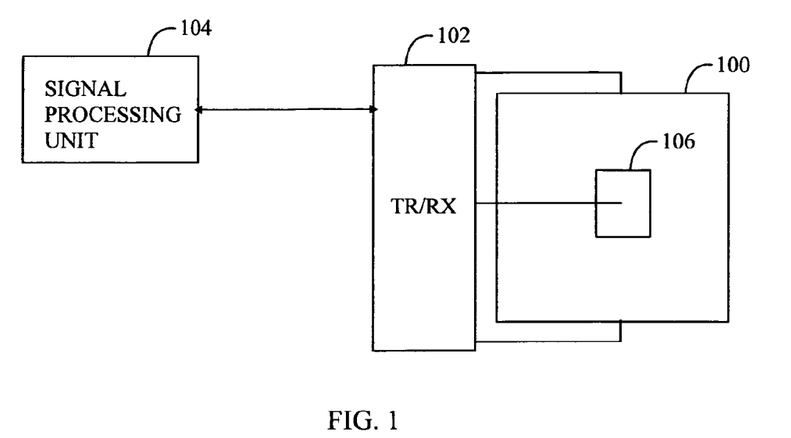
FIG. 1 is a block diagram showing a measurement device.

Radio frequency electromagnetic radiation may be used for measuring moisture from a direction-dependent material. FIG. 1 is a block diagram showing a measurement device comprising a measurement chamber 100, an electromagnetic field tuning and detection apparatus 102, and a signal processing unit 104. The measurement chamber 100 comprises walls that are at least partly made of an electrically conductive material, such as metal. The electrically conductive material encloses a three-dimensional space in to which an electromagnetic field is generated and in which resonance is formed. The measurement chamber 100 may be provided with one or more apertures whose maximum dimension is less than a measurement wavelength, and usually the size of each aperture is clearly smaller than half the wavelength.

The electromagnetic field tuning and detection apparatus 102 generates the radio frequency electromagnetic fields in to the measurement chamber 100 at least in two different directions. The electromagnetic field tuning and detection apparatus 102 may generate the radio frequency electromagnetic fields in to the measurement chamber 100 at least in two orthogonal or nearly orthogonal directions.

In FIG. 1, the directions may be e.g. horizontally from left to right (or vice versa), vertically, and perpendicularly through the figure in the viewing direction. At the time of measurement, the material to be measured resides in the measurement chamber 100, which may be provided e.g. with a material space 106 for the material. In the measurement chamber 100, radiation interacts with the material at the time of measurement.

The measurement chamber 100 may have the shape of a cube or a diamond, for instance, such that in each measurement direction, distances between a tuning switching element and a detecting switching element differ in length. Generally, the shape of the measurement chamber 100 is not limited to any shape as long as the shape enables measurement to take place at least in two different directions.

The signal processing unit 104 is connected to the electromagnetic field tuning and detection apparatus 102, which detects an electromagnetic field in the measurement chamber 100. The signal processing unit 104 enables the resonances of the electromagnetic field to be determined in each orthogonal direction. Thus, the signal processing unit 104 may determine a moisture content of a material on the basis of the frequency of each electromagnetic field in the resonance of the measurement chamber 100 and the quality of each resonance in the orthogonal directions.

Figure 2:
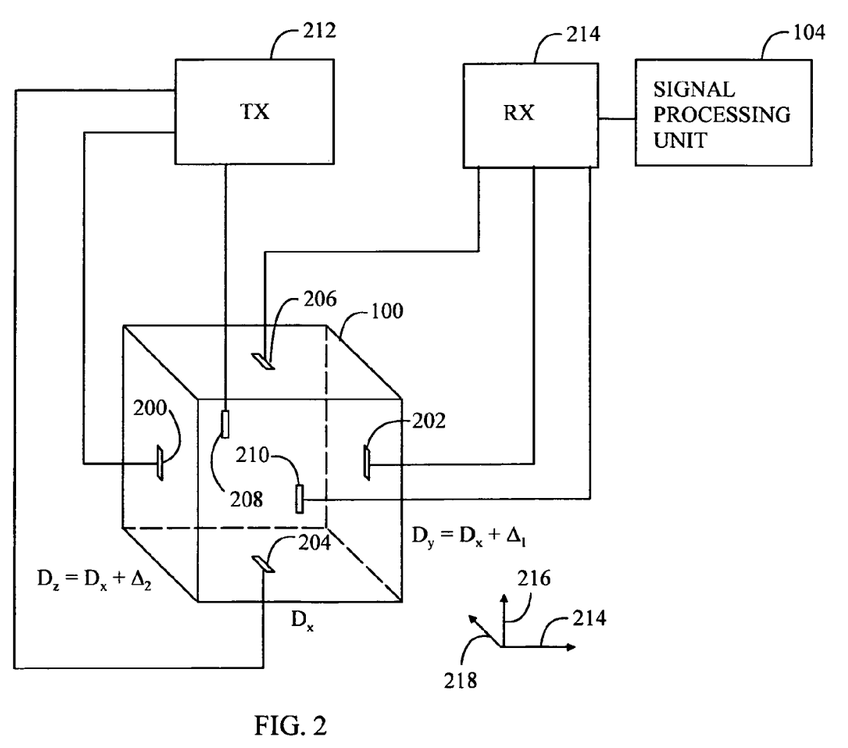
FIG. 2 shows a measurement chamber and an electromagnetic field tuning and detection apparatus.

FIG. 2 shows the measurement chamber 100 and the electromagnetic field tuning and detection apparatus 102 in closer detail. The electromagnetic field tuning and detection apparatus 102 comprises an electromagnetic energy source 212 and at least four switching elements 200 to 210. The switching elements 200 to 210 may be positioned on the sides of the cubical measurement chamber 100, enabling measurements to be carried out in at least two different directions. Half of the switching elements 200 to 210 may be switching elements 200, 204, 208 tuning an electromagnetic field while half thereof may be switching elements 202, 206, 210 detecting an electromagnetic field. The switching elements 200 to 210 may be any kind of switching elements that are used for generating and detecting a radio frequency electromagnetic field. The switching elements 200 to 210 may be e.g. monopoles, slot antennas, loop antennas, etc. The radio frequency electromagnetic energy source 212 feeds energy to the tuning switching elements 200, 204, 208, whereby an electromagnetic field is generated in the measurement chamber 100. The detecting switching elements 202, 206, 210, in turn, detect the electromagnetic field in different directions, which is received by a receiver 214. The receiver 214 relays a signal from the detected field to a signal processing unit 104. In such a case, for example, the tuning switching element 200 generates an electromagnetic field in to the measurement chamber 100 and the detecting switching element 202 detects the electromagnetic field of the measurement chamber 100 parallelly with the vector 214 or perpendicularly to the direction of the vector 214, depending on the switching manner. In this example, the vectors 214, 216, 218 are orthogonal with respect to one another. Correspondingly, the tuning switching element 204 generates an electromagnetic field in to the measurement chamber 100 and the detecting switching element 206 detects the electromagnetic field of the measurement chamber 100 parallelly with the vector 216 or perpendicularly to the direction of the vector 216, depending on the switching manner. Further, the tuning switching element 208 generates an electromagnetic field in to the measurement chamber 100 and the detecting switching element 210 detects the electric field of the measurement chamber 100 parallelly with the vector 218 or perpendicularly to the direction of the vector 218, depending on the switching manner. Each one of the detecting switching elements 202, 206, 208 is thus configured to detect the electromagnetic field of the corresponding at least one exciting switching element 200, 204, 208. When fields that are orthogonal with respect to one another are used, the fields do not become switched with one another in any significant degree. However, it is possible that each detecting switching element 202, 206, 210 detects the electromagnetic fields of other exciting switching elements as well, particularly when different switching elements are used.

Figure 3:
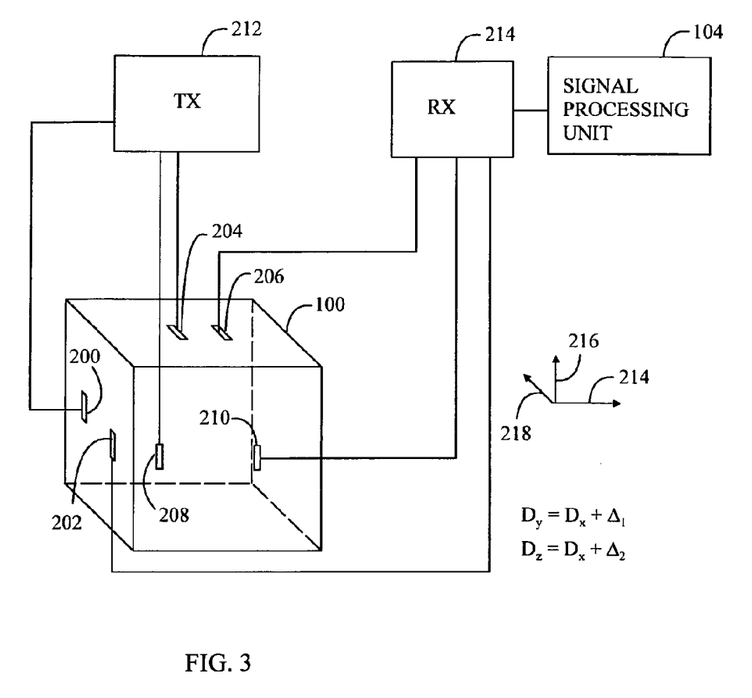
FIG. 3 shows a measurement chamber wherein a tuning switching element and a detecting switching element that are matched with one another are provided on the same side.

Instead of each matched tuning and detecting switching element pair being positioned on opposite sides of the measurement chamber 100 with respect to one another, as shown in FIG. 2, the tuning and detecting switching element pair may also be positioned on the same side of the measurement chamber 100, as shown in FIG. 3.

It is possible that the tuning switching elements 200, 204, 208 also operate as detecting switching elements. In such a case, no separate detecting elements 202, 206, 210 are necessary. The direction in which the switching elements 200, 204, 208 feed to the measurement chamber 100 and the direction in which they detect from the measurement chamber may thus be separated from one another e.g. by a circulator or a directional switch in order to enable measurement.

Generally at least some of the switching elements 200 to 210 are configured to excite the electromagnetic fields in the measurement chamber 100 in three orthogonal directions, and at least some of the switching elements 200 to 210 are configured to detect the electromagnetic fields in said three orthogonal directions.

Figure 4:
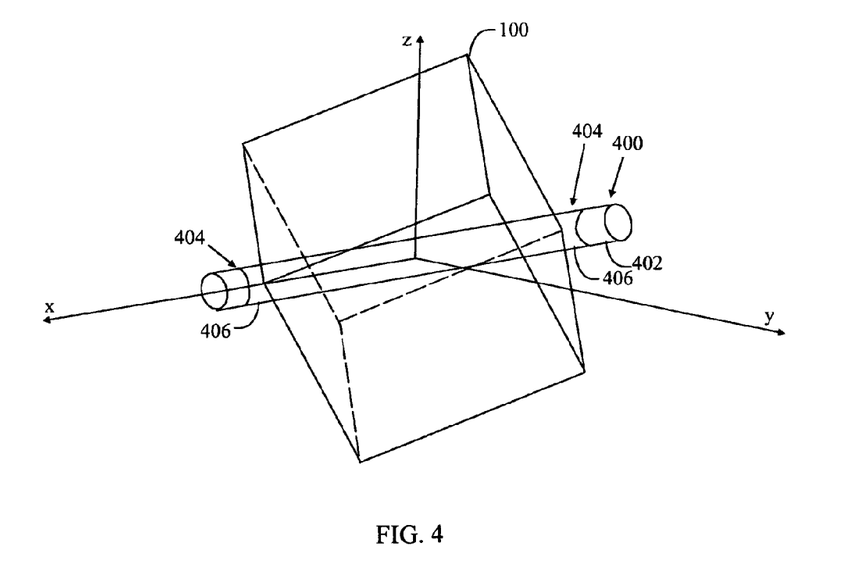
FIG. 4 shows a material space wherein a material to be measured flows.

FIG. 4 shows an embodiment wherein a material to be measured may flow through the measurement chamber 100 in a material space 400, which is e.g. tubular. The material space 400 comprises electrically non-conductive walls 402 in order for the walls 402 to be permeable to radio frequency electromagnetic radiation and in order for the walls not to interfere with the measurement. The walls 402 may be made from plastic, ceramics, etc. The measurement chamber 100 comprises apertures 404 for the material space 400. The edges of the apertures 404 may be provided with projections 406 made from an electrically conductive material for extinguishing the electromagnetic field in the material space which extends outside the measurement chamber 100. The projections 406 may be made e.g. from metal. In the example of FIG. 4, the material space 400 having the shape of a straight tube is arranged diagonally between the two most distant corners of the cubical measurement space 100. According to FIG. 2, the switching elements 200 to 210 may be positioned at the sides of the cubical measurement chamber 100. Vectors x, y, and z designate measurement directions and are parallel with the normals of the sides of the measurement chamber 100.

Figure 5:
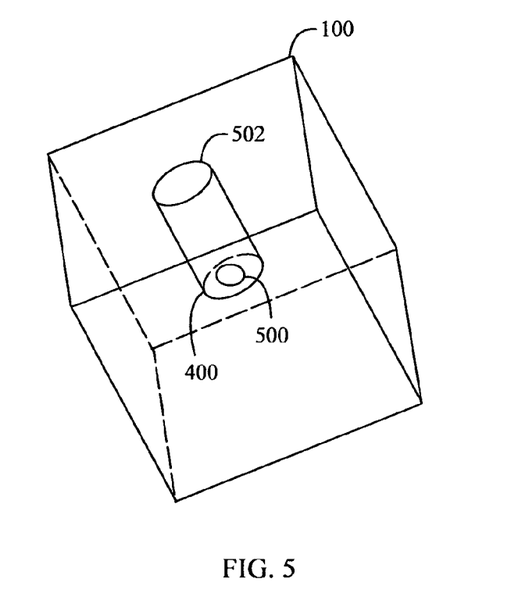
FIG. 5 shows a material space provided with a container.

FIG. 5 shows an embodiment wherein, instead of a tubular material space, the material space 400 is an open or closable container wherein a material 500 may be inserted for the duration of measurement. Also in this solution, the measurement chamber 100 has an aperture 502 to enable the material to be inserted into the material space 400. Both generally and in the situation of FIG. 5, the radio frequency electromagnetic fields may resonate at least in two different directions at a different frequency on the basis of the material 500 insertable into the material space 400.

Figure 6:
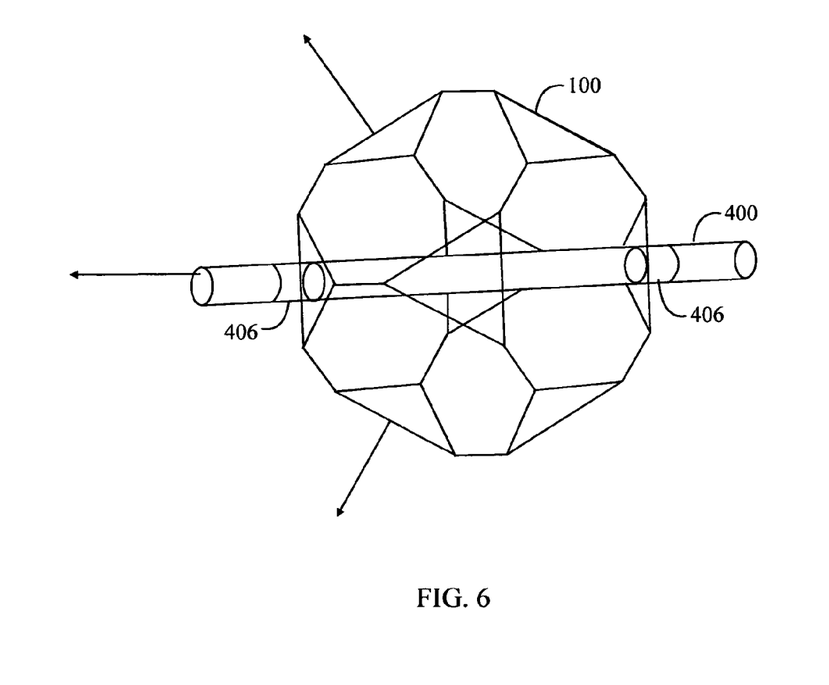
FIG. 6 shows a diamond-shaped measurement chamber.

FIG. 6 shows a diamond-shaped measurement chamber 100. Vectors x, y, and z designate measurement directions. In this example, one measurement direction x is parallel with the longitudinal axis of the tubular material space 400 and thus also with the main flow direction of the material in the tubular material space 400. In directions x, y, and z of different dimensions, diagonals $D_x$, $D_y$, and $D_z$ of the diamond may differ in length. In such a case, diagonal $D_y = D_x + \Delta_1$ and diagonal $D_z = D_x + \Delta_2 = D_y + \Delta_3$, i.e. the length D of the measurement chamber 100, is different in different directions. Each of differences $\Delta_1$, $\Delta_2$, and $\Delta_3$ may be equal or different in size and have a size e.g. of less than 25% of the wavelength $\lambda$ used, if at least two measures $D_x$ and $D_y$, $D_x$ and $D_z$, $D_y$ and $D_z$ or $D_x$, $D_y$ and $D_z$ used in the measurement are mutually different from one another. Differences $\Delta_1$, $\Delta_2$, and $\Delta_3$ may have a size e.g. of a couple of millimetres or at the most a couple of centimetres or a couple of tens of centimetres. Measures $D_x$, $D_y$, and $D_z$ may be a couple of tens of centimeters, for instance.

Figure 7:
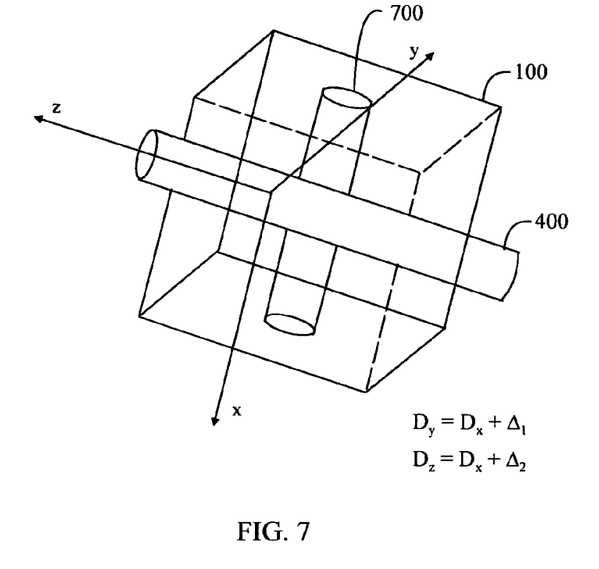
FIG. 7 shows a cubical measurement chamber.

FIG. 7 shows a cubical measurement chamber 100 whose sides parallel with the different dimensions x, y, and z differ in length, i.e. the length of the measurement chamber 100 is different in different dimensions. In a manner similar to that in connection with the diamond, the size of side $D_y$ is $D_y = D_x + \Delta_1$ and the size of side $D_z$ is $D_z = D_x + \Delta_2 = D_y + \Delta_3$, i.e. the length D of the measurement chamber 100 is different in different directions. Each $\Delta_1$, $\Delta_2$, and $\Delta_3$ may be equal or different in size and have a size of e.g. less than 25% of the wavelength $\lambda$ used. The measurement chamber 100 may be penetrated by a tubular material space 400 which extends from side to side thereof. The measurement may be carried out such that one measurement direction is parallel with the longitudinal axis of the tubular material space 400. Other measurement directions are parallel with the normals of the sides of the cubical measurement space 100.

The measurement chamber 100 may be filled with a foamed and electrically non-conductive material, such as foamed plastic. The plastic used may be e.g. polyurethane or expanded polystyrene. Foaming enables the relative dielectric constant of the material to be made nearly equal to the di-electric constant of air. The filling material does not necessarily require any separate tube but the tubular material space 400 may be a cavity in the material filling up the measurement chamber 100. Samples of the material to be measured may move in the tubular material space 400 e.g. by means of a conveyor belt, as a continuous flow, or the separate samples may be placed in sample vials carried by the conveyor belt. The use of a conveyor belt enables online measurements. The longitudinal axis of the cavity-like material space 400 may be straight or curved.

Generally it may be stated that in measurement chambers 100 having the above-described shape, the electromagnetic field is uniform at least at the material space, which contributes to reliable measurement. The electromagnetic field may be made even more uniform in different measurement directions by using one or more cavities 700, each cavity 700 being at least in one direction other than in the actual flow direction of a material sample. The cavities 700 may be in two directions orthogonal with respect to the direction of the actual material space 400, or in a direction and position otherwise correcting the measurement. The best positions and directions may be determined by test measurements. Each cavity 700 is a space having no material samples positioned or movable therein, but it may be useful if such a cavity 700 is filled with a dielectric material whose electric properties are close to those of the material to be measured.

A distance between inner surfaces of the walls of the measurement chamber 100 in a direction of the normal of the inner surface of a wall may be e.g. half the wavelength of the radiation used in the measurement, or a multiple thereof. In mathematical terms it may be expressed $L = n\lambda/2$, where n is a positive integer. On the other hand, a measurement device may employ a wavelength which is larger than a piece size of the material in order for radiation scattering from the pieces to be low. The measurement frequency may be less than 1 GHz or even less than 500 MHz if the largest measure of the pieces of the material to be measured is in the order of a couple of centimetres. If, again, the pieces or particles are small, the measurement frequency may be more than 1 GHz. A rule of thumb might be that the wavelength of the radiation used in the measurement has to be at least e.g. about 5 to 10 times larger than the largest measure of the pieces of the material on average.

At high moisture contents, a radio wave may find its way round the material to be measured in certain circumstances, in which case in resonator measurements the Q value, which should become smaller, may start to increase as moisture increases. In order to prevent this, the material may be subjected to radio frequency electromagnetic radiation such that the radiation is no longer capable of circumventing the material to be measured. In an embodiment, the waveform is selected such that the electromagnetic radiation penetrates into the material to be measured. In an embodiment, an electrically conductive material is arranged around the material to be measured to prevent the electromagnetic radiation from circumventing the material to be measured.

Figure 8:
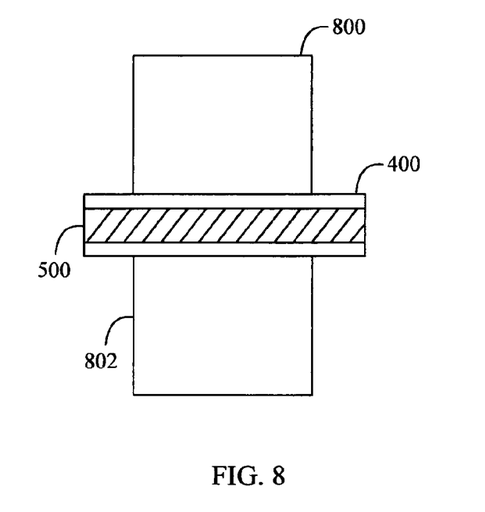
FIG. 8 shows two resonators directed at one another.

FIG. 8 shows a structure wherein measurements in different directions carried out by electromagnetic radiation may be implemented such that the electromagnetic radiation does not circumvent a sample. A resonator structure may comprise two resonator parts 800, 802 aligned with one another. The resonator parts 800, 802 may be cylindrical, square or rectangular hollow structures between which the material space 400 with or without the material 500 to be measured may be located. The resonator parts 800, 802 may be filled with a dielectric material, such as plastic or ceramics. The material space 400 may have the shape of a rectangular or a square or it may be a circular cylinder piece. The material 500 to be measured may be moulded into a flat shape and positioned between the resonator parts 800, 802 such that the electric field cannot circumvent the material 500.

Figure 10:
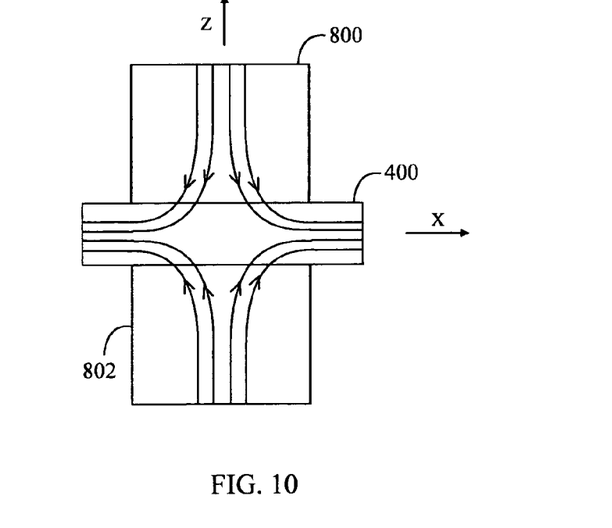
FIG. 10 shows an electric field formed by resonators when switching elements are used at ends of the resonators.
Figure 11:
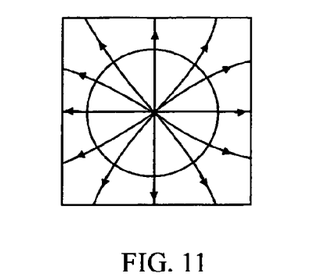
FIG. 11 is a top view of the electric field of FIG. 10.
Figure 12:
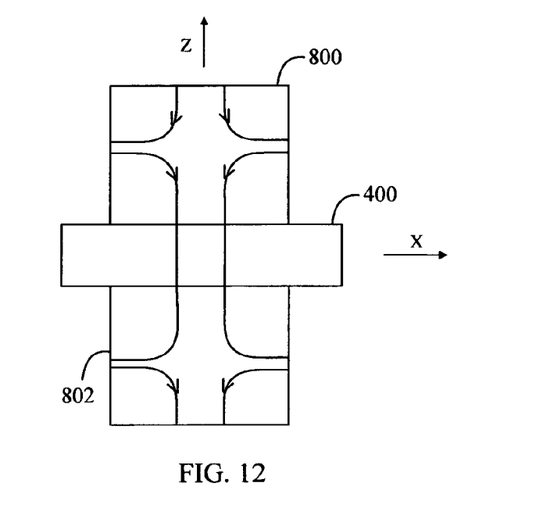
FIG. 12 shows an electric field generated by a different multiple of a TM waveform when switching elements are used at ends of resonators.

The material 500 to be measured may be subjected to electromagnetic fields of different directions by using different waveforms by changing the switching manner. For feeds and reception, monopoles may be used, but feeds may also be implemented by a switching loop by a slot feed or in another switching manner. By switching in accordance with FIG. 9 the electric field from an end of the resonator by a monopole 900, a waveform according to either FIG. 10 or FIG. 12 is achieved, depending on the multiple of the TM waveform of the material 500. FIG. 11 shows the waveform of FIG. 10 from above. In the solution according to FIGS. 10 and 11, the resonator consisting of the resonator parts 800, 802 and the material space 400 may be open or closed. In a closed solution, the edges of the material space 400 or the material 500 to be measured are provided with an electrically conductive material, i.e. the boundaries of a measurement area are shorted out. In an open solution, no electrically conductive material is used for restricting the electromagnetic field. The waveform of FIG. 10 simultaneously has fields both in x and y directions, and in the case of FIG. 12, a field in direction z. In the embodiment of FIG. 12, the resonator is usually open, but it may also be used as a closed one. In the case of FIG. 12, the feed and reception elements may also be placed side by side in the same resonator.

Figure 9:
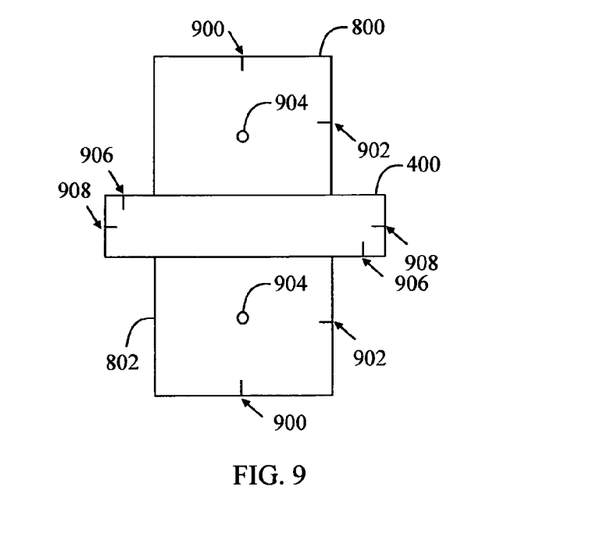
FIG. 9 shows positions of switching elements of resonators.
Figure 13:
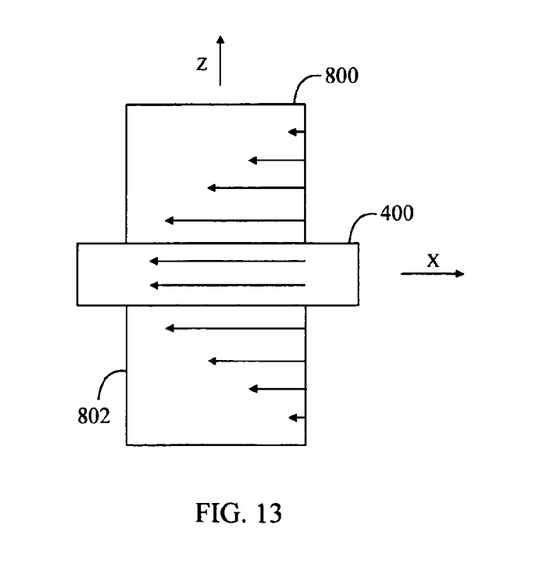
FIG. 13 shows an electric field generated by resonators when switching elements are used at a side of resonators.

By switching the electric field in accordance with FIG. 9 by a monopole 902, an electric field according to FIG. 13 and according to a TE waveform is obtained in direction x; and, correspondingly, by switching it by a monopole 904, a field in direction y is obtained. The solution of FIG. 13 operates as an open configuration. A solution similar to that of FIG. 13 is one wherein the electric field is parallel with the y-axis. Correspondingly, the monopole may be provided in accordance with FIG. 9 or side by side in the same resonator part or oppositely on the other side of the resonator.

Figure 14:
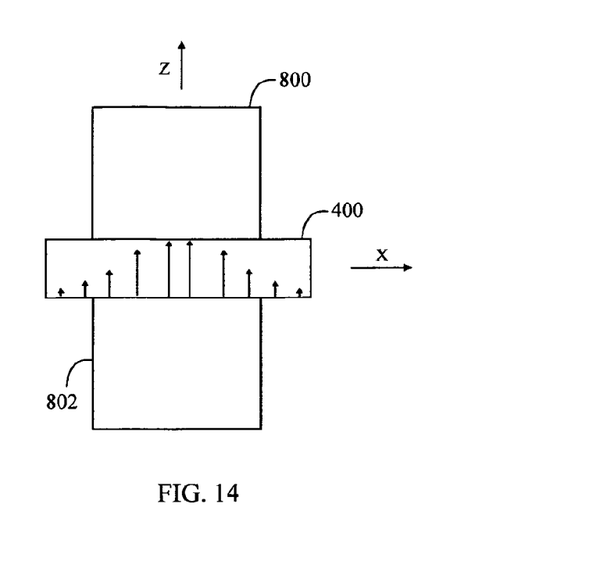
FIG. 14 shows an electric field generated by resonators when switching elements are used at different ends of a measurement space.

By switching the electric field in accordance with FIG. 9 by a probe 906, an electric field is obtained in direction z in the measurement area, according to FIG. 14. In the embodiment of FIG. 14, the resonator may operate as a closed configuration. Such a closed resonator prevents the electromagnetic field from circumventing the material 500 contained in the material space 400.

By switching the electric field in accordance with FIG. 9 by a probe 908, a selective electric field is obtained in the measurement area, which is in accordance with FIG. 10 but not in accordance with FIG. 12.

In an embodiment, the transmitting side and the receiving side may be placed on different sides of the material 500 in order to ensure that it is the transmittance resonance rather than one-sided reflection resonance that becomes measured. According to FIG. 8, the measurement chamber may be closed in each direction on a conductive wall. In an online implementation, two walls may be opened to allow a material flow to pass through. Also, all walls may be removed if the material to be measured is planar/platelike, in which case it is impossible for the radio frequency radiation to circumvent the sample.

Generally it may be stated that if the shape of the material to be measured is planar, whereby its dimensions mainly reside in two directions, measurement in two directions will suffice. If the material to be measured is clearly three-dimensional, measurement may be carried out from three different directions. A material to be measured is planar if a ratio of its two smallest orthogonal measures is less than 1:3. Alternatively, a material to be measured may be determined to be planar if its aforementioned ratio is 1:5 or less. For instance, a board may have the following measures: length 2 m, width 0.1 m, and thickness 0.02 m. In such a case, the ratio of two smallest orthogonal measures is 0.02 m/0.1 m=0.2=1/5<1:3. Consequently, such a board may be considered planar and be measured by using measurement that is sensitive in two different directions.

Figure 15:
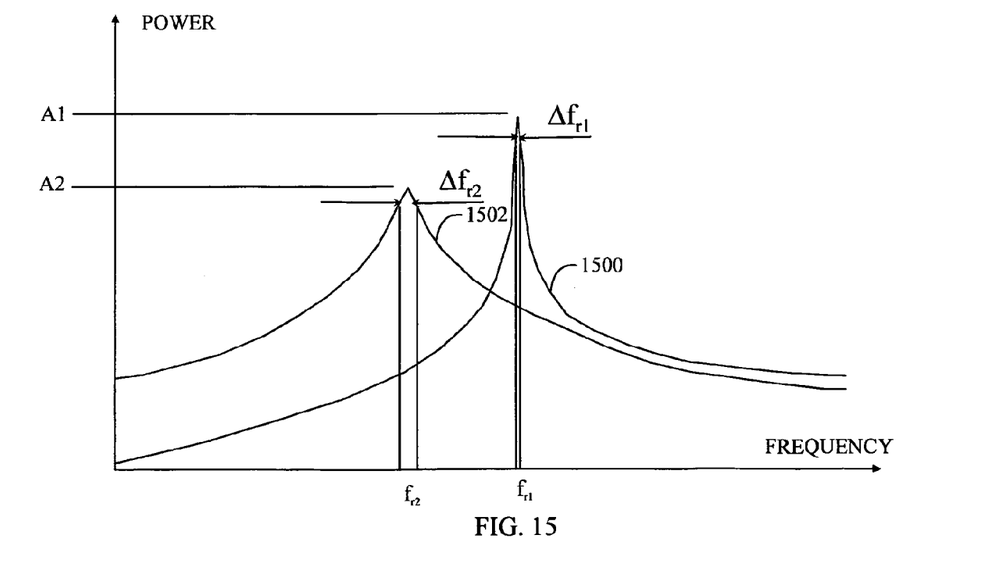
FIG. 15 is a line graph showing a strength of an electric magnetic field as a function of frequency.

In FIG. 15, a curve 1500 shows a strength A of an electromagnetic field in the measurement chamber 100 or in the material space 400 with no material to be measured while a curve 1502 shows the strength of an electromagnetic field 1502 as a function of frequency f in the measurement chamber with a material to be measured when measured from one direction. The strength A of a signal is shown on the vertical axis on a freely selected logarithmic scale while the frequency f of the signal is shown on the horizontal axis on a freely selected linear scale. The resonance of the measurement chamber 100 may be measured by sweeping the wavelength of the radio frequency electromagnetic energy source 212 over a predetermined band. In such a case, the predetermined band includes a resonance frequency. The signal processing unit 104 may measure the detected strength of the radio frequency radiation of the measurement chamber 100 as a function of frequency in order to determine a resonance frequency and a resonance quality. The resonance frequency $f_r$ is the frequency at which the detected electromagnetic field is at its strongest. On the curve 1500, the strength of the resonance frequency $f_{r1}$ is great and the resonance band $\Delta f_{r1}$ is narrow. On the curve 1502, the strength of the resonance frequency $f_{r2}$ is small and the resonance band $\Delta f_{r2}$ is wide. Generally expressed, two different materials usually have different resonance frequency $f_r$, strength A of resonance frequency $f_r$, and width of resonance band $\Delta f_r$. The width of the resonance band $\Delta f_r$ determines the quality of resonance and is often used for determining the quality of resonance.

The determination of the width of the resonance band may be based e.g. on the width of a band in which the efficiency of a measurement signal has dropped by 3 dB, i.e. about 50% of the maximum. The quality of resonance is indicated by a quality factor Q which may be calculated e.g. by equation $Q=f_r/\Delta f_r$. In addition to the moisture of the material, the measured parameters Q and $f_r$ are also affected by the density and amount of the material, whose influence may be compensated for in a calculatory manner. This makes it possible to measure only moisture from a material sample. The more dimensions in which the parameters Q and $f_r$ are measured, the more accurate the measurement of moisture becomes. The parameters Q and $f_r$ measured in the direction of each dimension may be averaged, for instance.

In addition to or instead of determining the width of the resonance band, the signal processing unit 104 may determine the quality of resonance also from the strength A of the resonance frequency. If resonance is generated by a freely oscillating oscillator which locks to the resonance with no frequency sweeping, it may be difficult to determine the resonance band width. In such a case, resonance band width determination may be replaced by measuring the resonance frequency strength.

Moisture K, which is independent of the measurement direction of the material to be measured, may be determined in each orthogonal direction as a function of the measured resonance frequencies and the quality thereof. Mathematically, the equation of moisture K may be expressed as follows:

$$K=f(f_{r1}, \Delta f_{r1}, f_{r2}, \Delta f_{r2}, f_{r3}, \Delta f_{r3}),$$

where $f_{r1}$ means the resonance frequency in a first orthogonal direction, $f_{r2}$ means the resonance frequency in a second orthogonal direction, $f_{r3}$ means the resonance frequency in a third orthogonal direction, $\Delta f_{r1}$ means the width of the resonance band in the first orthogonal direction, $\Delta f_{r2}$ means the width of the resonance band in the second orthogonal direction, and $\Delta f_{r3}$ means the width of the resonance band in the third orthogonal direction. The function f may also be determined theoretically, by simulation or experimentally. Moisture may also be expressed in the following manner:

$$K=f_1(f_{r1}, \Delta f_{r1})+f_2(f_{r2}, \Delta f_{r2})+f_3(f_{r3}, \Delta f_{r3});$$

herein, functions $f_2$, and $f_3$ may be determined theoretically, by simulation or experimentally.

The solution may even be deconstructed into the following form, wherein each function $f_i$ has been separated into two functions $f_{ij}$ in the following manner:

$$K=f_{11}f_{r1}+f_{12}\Delta f_{r1}+f_{21}f_{r2}+f_{22}\Delta f_{r2}+f_{31}f_{r3}+f_{32}\Delta f_{r3};$$

here, too, the functions $f_1$, $f_2$, and $f_3$ may be determined theoretically, by simulation or experimentally.

Further, moisture K may be expressed as linear dependencies by replacing functions $f_{11}$, $f_{12}$, $f_{21}$, $f_{22}$, $f_{31}$, and $f_{32}$ by coefficients $k_{11}$, $k_{12}$, $k_{21}$, $k_{22}$, $k_{31}$, and $k_{32}$.

$$K=f_{11}f_{r1}+f_{12}\Delta f_{r1}+f_{21}f_{r2}+f_{22}\Delta f_{r2}+f_{31}f_{r3}+f_{32}\Delta f_{r3};$$

herein, too, the coefficients $k_{11}$, $k_{12}$, $k_{21}$, $k_{22}$, $k_{31}$, and $k_{32}$ may be determined theoretically, by simulation or experimentally. Another purpose of the above-disclosed equations is to express that moisture may be determined, at least approximately, as a weighted average of resonance frequencies in different directions, wherein the bandwidth of resonance (or the amplitude of resonance) is also taken into account, appropriately weighted. Further, the value of moisture may be made more precise as an average of several successive measurements.

Density T of the material to be measured may be determined in an exactly corresponding manner. The linear dependence of density on frequency and resonance bandwidth may be expressed e.g. in the following manner:

$$T=p_{11}f_{r1}+p_{12}\Delta f_{r1}+p_{21}f_{r2}+p_{22}\Delta f_{r2}+p_{31}f_{r3}+p_{32}\Delta f_{r3};$$

where coefficients p may be determined theoretically, by simulation or experimentally. In all cases, the resonance band width $\Delta f_{r1}$, $\Delta f_{r2}$, $\Delta f_{r3}$ may be replaced by resonance amplitude $A_{r1}$, $A_{r2}$, $A_{r3}$ or a combined influence thereof $g(\Delta f_{r1}, \Delta f_{r2}, \Delta f_{r3}, A_{r1}, A_{r2}, A_{r3})$, where function g may be determined theoretically, by simulation or experimentally. When measurement is carried out in the direction of the tubular material space e.g. as a continuous flow, there is more material in the direction of the tube than in other directions. This difference may also be taken into account in the weighting coefficients or functions used in the calculation.

Figure 16:
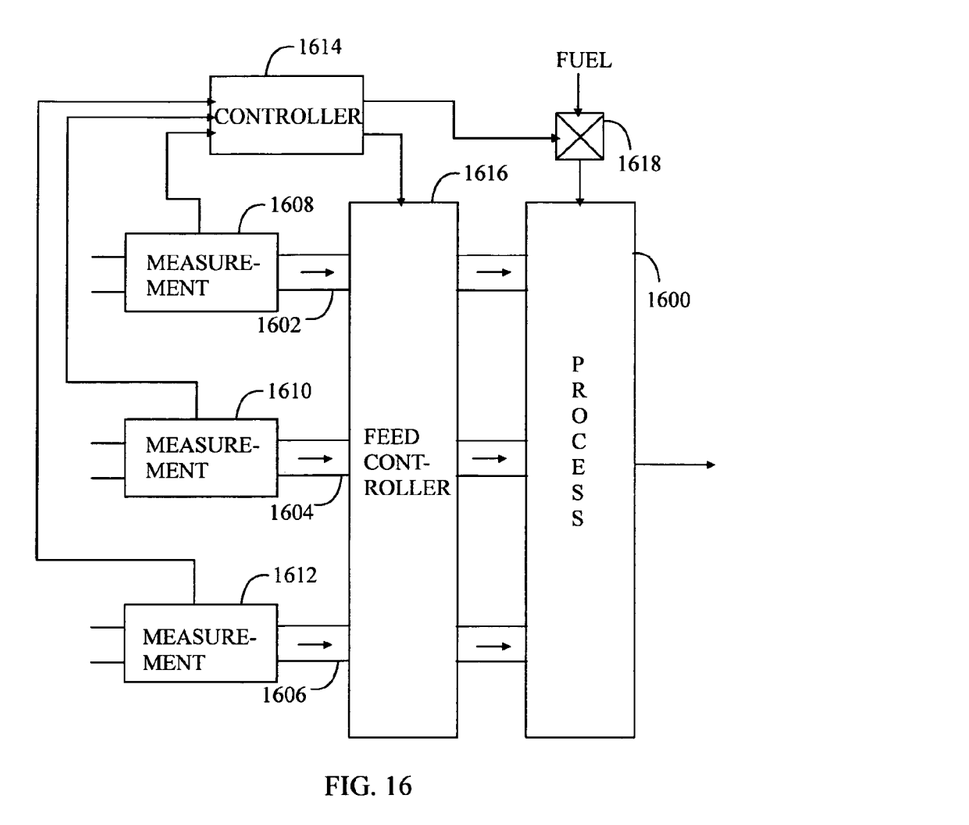
FIG. 16 shows process control.

FIG. 16 shows process control. A material is fed to a process 1600 by three feed lines 1602, 1604, 1606. The process 1600 may be e.g. a burning process to which is fed a burning material, such as biomaterial, e.g. chips, sawdust, cuttings, bark, peat, various biowaste, etc. The moisture content of the material on each feed line 1602, 1604, 1606 may be measured by measuring devices 1608, 1610, 1612 in the above-described manner, and moisture data of each feed line 1602, 1604, 1606 may be fed to a controller 1614. The controller 1608 may control the material feed on each feed line 1602, 1604, 1606 in a proportion reverse to the moisture content of the feed line 1602, 1604, 1606. In such a case, the controller 1608 controls an actuator 1616 which controls the feed amount of each feed line 1602, 1604, 1606 and which, according to a control command from the controller 1608, may increase, maintain or decrease the amount of material fed by each feed line 1602, 1604, 1606 to the process 1600. If the feed lines 1602, 1604, 1606 are conveyor belts or the like, the actuator 1616, which may be a motor, such as an electric motor, may increase, maintain or decrease the speed of the conveyor belts in order to change the amount of material feed-line-specifically. The controller 1614 may restrict the material feed from a feed line 1602, 1604, 1606 on which the material has a moisture content not exceeding a predetermined danger threshold. In such a case, the material is too dry and may cause an explosion hazard, for instance. The controller 1614 may decrease the material feed from at least one feed line 1602, 1604, 1606 whose moisture content exceeds a predetermined threshold value. In such a case, the material is too damp or wet, which may deteriorate the operation of the process 1600. For example, the efficiency of the burning process is reduced.

When the process 1600 is a burning process of the material, the controller 1614 may add fuel to the burning process when the moisture content of the material is at a predetermined limit or when it exceeds a predetermined limit. In such a case, the controller 1614 may control an actuator 1618, which may be a valve, to allow more fuel, such as fuel oil, to the process. Similarly, the controller 1614 may decrease the amount of fuel in the burning process when the moisture content of the material is below a determined limit. The controller 1614 may then control the actuator 1618, which may be a valve, to decrease the fuel feed to the process.

Moisture measurements are necessary owing to a plurality of reasons. Variations in the moisture content of materials to be burned in energy production hinder burning and decrease the efficiency of energy production. Too dry a material, in turn, may cause e.g. an explosion hazard. In addition, pricing the material to be burned is based on the energy it produces, which depends on the moisture content of the material.

Figure 17:
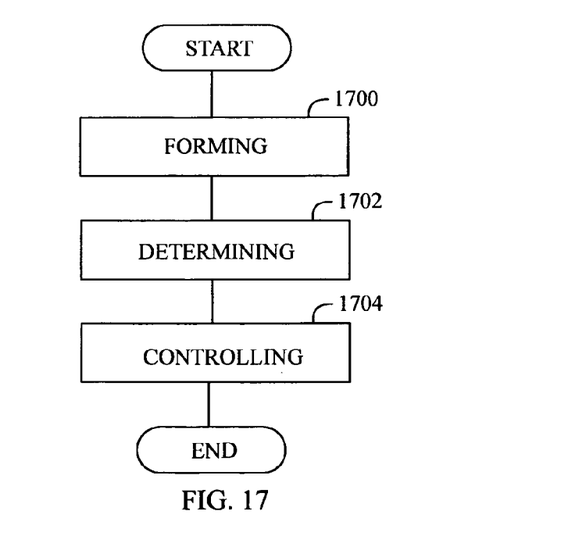
FIG. 17 is a flow diagram of a measurement and control method.

FIG. 17 is a flow diagram showing a measurement and control method. In step 1700 of the measurement, radio frequency electromagnetic fields are generated in at least two different directions, such electromagnetic fields resonating in different directions at a different frequency on the basis of the material insertable into the material space. In step 1702, a moisture content of the material is determined based on the resonance frequency of each electromagnetic field and on the quality of each resonance in orthogonal directions. The method of controlling a process further comprises step 1704 wherein the process is controlled based on each determined moisture content on each feed line.

The method shown in FIG. 17 may be implemented as a logic circuit solution or as a computer program. The computer program may be situated in a computer program distribution device for distribution thereof. The computer program distribution device is readable by a data processing device and it encodes computer program commands to control the operation of a performance measurement system.

The distribution device, in turn, may be a solution known per se for distributing a computer program, e.g. a medium readable by a data processing device, a program storage medium, a memory readable by a data processing device, a software distribution package readable by a data processing device, a signal readable by a data processing device, a data communications signal readable by a data processing device or a compressed software package readable by a data processing device.

Although the invention has been described above with reference to the examples according to accompanying drawings, it is clear that the invention is not restricted thereto but may vary in many ways within the scope of the attached claims.

What is claimed is:

1. A measurement device for measuring moisture from a material by electromagnetic radiation, wherein the measurement device comprises:
    a closed material space;
    a resonator with a first resonator part and a second resonator part, the resonator parts being aligned with one another, the material space being between the resonator parts and the material to be measured being insertable into the material space;
    the resonator parts comprising a generating element in the first resonator part and a detecting element in the second resonator part, the generating element and the resonator parts generating a resonating electric field which is vertical in the resonator parts and laterally omnidirectional in the material space; and
    a signal processing unit configured to determine a moisture content of the material based on a resonance frequency of an electromagnetic omnidirectional waveform resulting from the resonating electric field.

2. A device as claimed in claim 1, wherein the first resonator part and second resonator part are adapted to be placed on opposite sides of the material space.

3. A device as claimed in claim 1, wherein the measurement device is configured to generate the resonating electric field at least in two orthogonal directions.

4. A device as claimed in claim 1, wherein when the material to be measured is planar, the measurement device is configured to generate the resonating electric field in to the material space in two different directions.

5. A device as claimed in claim 1, wherein when the material to be measured is three-dimensional, the measurement device being configured to generate the resonating electric field in to the material space at least in three different directions.

6. A device as claimed in claim 1, wherein the resonating electric field are adapted to resonate at a different frequency in different directions on the basis of dimensions of the material space that are different in different directions.

7. A device as claimed in claim 1, wherein the resonating electric field is adapted to resonate at a different frequency in different directions on the basis of different waveforms in different directions.

8. A device as claimed in claim 1, wherein the measurement device comprises a radiation source and at least three switching elements, including the generating element and the detecting element, at least some of the switching elements being configured to excite the resonating electric field in different directions, at least some of the switching elements being configured to detect the resonating electric field in said directions.

9. A device as claimed in claim 8, wherein the measuring device comprises at least three exciting switching elements including the generating element and at least three detecting switching elements including the detecting element, each of the detecting switching elements being tuned to detect the resonating electric field of one exciting switching element.

10. A device as claimed in claim 1, wherein the resonating electric field has a radio frequency, and the measuring device is configured to sweep the frequency over a predetermined band, the signal processing unit being configured to measure a strength of the radio frequency radiation as a function of frequency in order to determine a resonance frequency and a resonance quality.

11. A device as claimed in claim 1, wherein the measurement device is configured to use a wavelength that is greater than a piece size of the material.

12. A control system for controlling a process which receives a material whose moisture content varies, wherein the control system comprises:
    a resonator positioned on each feed line of one or more feed lines of the process, each resonator including a first resonator part and a second resonator part, the resonator parts being aligned with one another, a closed material space being positioned between the resonator parts and the material to be measured being insertable into the material space;
    the resonator parts comprising a generating element in the first resonator part and a detecting element in the second resonator part, the generating element and the resonator parts generating a resonating electric field which is vertical in the resonator parts and laterally omnidirectional in the material space;
    a signal processing unit configured to determine a moisture content of the material on each feed line based on a resonance frequency of an electromagnetic omnidirectional waveform resulting from the resonating electric field; and
    a controller configured to control the process on the basis of each determined moisture content on each feed line.

13. A system as claimed in claim 12, wherein the measuring device is configured to generate the resonating electric field at least in two orthogonal directions.

14. A system as claimed in claim 12, wherein the process is a material burning process.

15. A system as claimed in claim 14, wherein the controller is configured to add fuel to the burning process when the moisture content of the material is at a predetermined limit or when it exceeds a predetermined limit, the controller being configured to decrease fuel in the burning process when the moisture content of the material is below a predetermined limit.

16. A system as claimed in claim 12, wherein the controller is configured to restrict a material feed from a feed line whose moisture content is below a predetermined danger threshold.

17. A system as claimed in claim 12, the controller is configured to control the material feed on each feed line in a proportion reverse to the moisture content of the feed line.

18. A system as claimed in claim 12, wherein the controller is configured to decrease the material feed from at least one feed line whose moisture content exceeds a predetermined threshold value.

19. A method of measuring moisture from a material by radio frequency electromagnetic radiation, the method comprising:

generating, by a generating element and resonator parts, a resonating electric field which is vertical in the resonator parts and laterally omnidirectional in a closed material space disposed between the resonator parts, the material space being configured for a material to be measured to be insertable into the material space, the resonator parts being aligned with one another and including a first resonator part and a second resonator part, the resonator parts further comprising a generating element in the first resonator part and a detecting element in the second resonator part; and determining a moisture content of the material based on a resonance frequency of an electromagnetic omnidirectional waveform resulting from the resonating electric field.

20. A method as claimed in claim 19, the method further comprising generating the resonating electric field at least in two orthogonal directions.

21. A method as claimed in claim 19, the method further comprising generating the resonating electric field in to the material space in two different directions when the material to be measured is planar.

22. A method as claimed in claim 19, the method further comprising generating the resonating electric field in to the material space at least in three different directions when the material to be measured is three-dimensional.

23. A method as claimed in claim 19, the method further comprising:

exciting the resonating electric field, by switching elements of the resonator parts, in different directions; and detecting the resonating electric field in said different directions by at least some of the switching elements, wherein an electromagnetic field tuning and detection apparatus comprises the generating element and at least two switching elements.

24. A method as claimed in claim 23, wherein the switching elements of the electromagnetic field tuning and detection apparatus include at least three generating elements and at least three detecting elements, each of the detecting elements being tuned to detect the resonating electric field of one of the exciting switching elements.

25. A method as claimed in claim 19, the method further comprising:

sweeping a frequency of radio frequency radiation over a predetermined band by the electromagnetic field tuning and detection apparatus; and measuring a strength of the radio frequency radiation as a function of frequency by a signal processing unit in order to determine a resonance frequency and a resonance quality.

26. A method as claimed in claim 19, the method further comprising carrying out measurement at a wavelength that is greater than a piece size of the material.

27. A method of controlling a process which receives a material whose moisture content varies, the method comprising:

generating, by a generating element and resonator parts, a resonating electric field which is vertical in the resonator parts and laterally omnidirectional in a closed material space disposed between the resonator parts, the material space being configured for a material to be measured to be insertable into the material space, the resonator parts being aligned with one another and including a first resonator part and a second resonator part, the resonator parts further comprising a generating element in the first resonator part and a detecting element in the second resonator part;

determining the moisture content of the material based on a resonance frequency of an electromagnetic omnidirectional waveform resulting from the resonating electric field; and controlling the process on the basis of each determined moisture content on each feed line of one or more feed lines of the process.

28. A method as claimed in claim 27, the method further comprising generating the resonating electric field at least in two orthogonal directions.

29. A method as claimed in claim 27, wherein the process is a material burning process.

30. A method as claimed in claim 29, the method further comprising:

adding fuel to the burning process when the moisture content of the material is at a predetermined level or when it exceeds a predetermined limit; and decreasing fuel in the burning process when the moisture content of the material is below a predetermined limit.

31. A method as claimed in claim 27, the method further comprising restricting a material feed from a feed line of the process whose moisture content is below a predetermined danger threshold.

32. A method as claimed in claim 27, the method further comprising controlling the material feed on each feed line in a proportion reverse to the moisture content of the feed line.

33. A method as claimed in claim 27, the method further comprising decreasing the material feed from at least one of the feed lines of the process whose moisture content exceeds a predetermined threshold value.

* * * * *

UNITED STATES PATENT AND TRADEMARK OFFICE

CERTIFICATE OF CORRECTION

PATENT NO.       : 8,725,284 B2
APPLICATION NO.  : 13/503724
DATED            : May 13, 2014
INVENTOR(S)      : Jakkula et al.

Page 1 of 1

It is certified that error appears in the above-identified patent and that said Letters Patent is hereby corrected as shown below:

IN THE SPECIFICATION:

Column 9, line 51

Now reads:    "$K=f_{11}$";

Should read:    -- $K=k_{11}$ --.

Signed and Sealed this
Ninth Day of September, 2014

Michelle K. Lee
*Deputy Director of the United States Patent and Trademark Office*